United States Patent
Lee et al.

(10) Patent No.: US 9,260,401 B2
(45) Date of Patent: Feb. 16, 2016

(54) METHOD FOR PREPARING CABAZITAXEL FROM 10-DEACETYLBACCATIN III IN HIGH YIELD, AND NOVEL INTERMEDIATE THEREFOR

(71) Applicant: SAMYANG BIOPHARMACEUTICALS CORPORATION, Seoul (KR)

(72) Inventors: Na Young Lee, Daejeon (KR); Seong Ho Kim, Daejeon (KR); Young Min Kim, Daejeon (KR); Jin Suk Cho, Daejeon (KR); Moon Suk Kim, Daejeon (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 0 days.

(21) Appl. No.: 14/647,147

(22) PCT Filed: Dec. 3, 2013

(86) PCT No.: PCT/KR2013/011084

§ 371 (c)(1),
(2) Date: May 26, 2015

(87) PCT Pub. No.: WO2014/088281

PCT Pub. Date: Jun. 12, 2014

(65) Prior Publication Data

US 2015/0291545 A1    Oct. 15, 2015

(30) Foreign Application Priority Data

Dec. 4, 2012 (KR) .................. 10-2012-0139485

(51) Int. Cl.
*C07D 305/14* (2006.01)
*A61K 31/337* (2006.01)
*C07D 413/12* (2006.01)
*C07F 7/18* (2006.01)

(52) U.S. Cl.
CPC ............ *C07D 305/14* (2013.01); *A61K 31/337* (2013.01); *C07D 413/12* (2013.01); *C07F 7/1844* (2013.01); *C07F 7/1856* (2013.01)

(58) Field of Classification Search
CPC .................................................... C07D 305/14
USPC .......................................................... 549/214
See application file for complete search history.

(56) References Cited

U.S. PATENT DOCUMENTS

| 5,962,705 | A | 10/1999 | Didier et al. |
| 6,331,635 | B1 | 12/2001 | Bouchard et al. |
| 2012/0149925 | A1 | 6/2012 | Kung et al. |

FOREIGN PATENT DOCUMENTS

| EP | 2 330 100 A1 | 6/2011 |
| KR | 2001-0032138 A | 4/2001 |
| WO | WO 96/30355 A1 | 10/1996 |
| WO | WO 99/25704 A1 | 5/1999 |

OTHER PUBLICATIONS

8 International Search Report, issued in PCT/KR2013/011084, dated Mar. 25, 2014.

*Primary Examiner* — Taofiq A Solola
(74) *Attorney, Agent, or Firm* — Birch, Stewart, Kolasch & Birch, LLP

(57) ABSTRACT

The present invention relates to a novel method for preparing cabazitaxel from 10-deacetylbaccatin III, and a novel intermediate therefor, and more specifically, to: a method which allows cabazitaxel to be more easily prepared in a high yield and in a high purity within a short time compared with a conventional method by preparing cabazitaxel via a novel intermediate using 10-deacetylbaccatin III as a starting material, and thus is suitable for industrial mass production; and a novel intermediate therefor.

14 Claims, No Drawings

METHOD FOR PREPARING CABAZITAXEL FROM 10-DEACETYLBACCATIN III IN HIGH YIELD, AND NOVEL INTERMEDIATE THEREFOR

TECHNICAL FIELD

An embodiment of the present invention relates to a method for preparing cabazitaxel from 10-deacetylbaccatin III and an intermediate therefor. More specifically, an embodiment of the present invention relates to a method which can easily prepare cabazitaxel in a high yield and purity within a short time as compared with conventional methods by the use of 10-deacetylbaccatin III as a starting material and via an intermediate, and thus is suitable for industrial-scale production, and an intermediate therefor.

BACKGROUND ART

Cabazitaxel, which has a chemical structure of the following Chemical Formula 1, is a material showing excellent anticancer activity, and its demand is increasing in industrial fields such as medicine. However, in spite of an increasing demand, preparation methods for cabazitaxel developed up to now have limitations in being very inefficient and having low productivity.

[Chemical Formula 1]

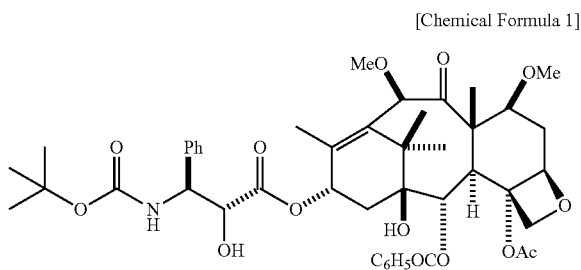

International Publication No. WO 96/30355 discloses a process for preparing cabazitaxel from 10-deacetylbaccatin via 6 steps. However, in this process the synthesis time required for synthesizing from a starting material to a final product is too long, about 109 hours. Specifically, step 3 (deprotecting step of silyl radical) has a shortcoming—an excessively long reaction time of 48 hours. Such a long reaction time is due to the protection and deprotection of hydroxy group at the 13 position. In addition, the final yield of the target compound, cabazitaxel, is about 4%, even though the synthetic process required such a long time. As a result, this process has a shortcoming in that it is difficult to apply it to a process for producing cabazitaxel on an industrial scale.

In addition, International Publication No. WO 99/25704 discloses a method for synthesizing cabazitaxel via a total of 3 steps from 10-diacetylbaccatin including simultaneous alkylation of hydroxy groups of the 7 and 10 positions of 10-diacetylbaccatin in a single step. However, this method also has a problem in that the final synthesis yield of cabazitaxel is only about 8%.

In summary, conventional methods are not suitable for industrial-scale production due to their inefficiency and low productivity. Therefore, there is strong demand for developing a novel method for preparing cabazitaxel which is more efficient and shows dramatically improved yield.

DISCLOSURE OF INVENTION

Technical Problem

The present invention is intended to solve the problems of the conventional methods as described above. The technical problem of the present invention is the provision of a method for easily preparing cabazitaxel in a high yield and purity within a short time with 10-deacetylbaccatin III as a starting material and an intermediate therefor.

Solution to Problem

To solve the above technical problem, an embodiment of the present invention provides a method for preparing cabazitaxel comprising the steps of:

1) reacting 10-deacetylbaccatin III of Chemical Formula 2 with a silylating agent to obtain an intermediate of Chemical Formula 3 in which hydroxy group at the 7 position is protected by a silylated radical;

2) methylating hydroxy group at the 10 position of the intermediate of Chemical Formula 3 to obtain an intermediate of Chemical Formula 4;

3) deprotecting hydroxy group at the 7 position of the intermediate of Chemical Formula 4 to obtain an intermediate of Chemical Formula 5;

4) methylating hydroxy group at the 7 position of the intermediate of Chemical Formula 5 to obtain an intermediate of Chemical Formula 6;

5) esterifying hydroxy group at the 13 position of the intermediate of Chemical Formula 6 in the presence of oxazolidine acid derivative of Chemical Formula 8 to obtain an intermediate of Chemical Formula 7; and 6) treating the intermediate of Chemical Formula 7 with an acid to obtain cabazitaxel of Chemical Formula 1:

[Chemical Formula 2]

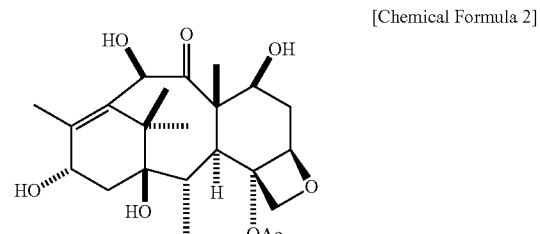

[Chemical Formula 3]

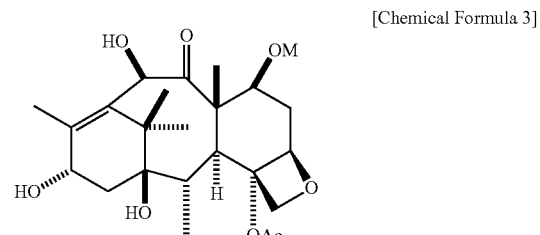

[Chemical Formula 4]

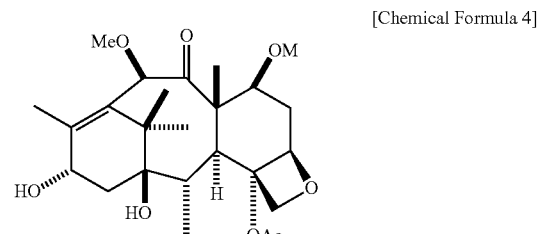

[Chemical Formula 5]

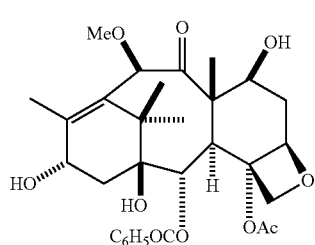

[Chemical Formula 6]

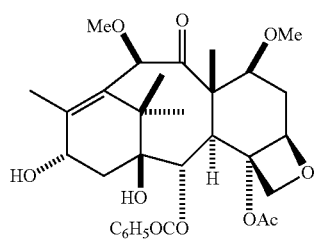

[Chemical Formula 7]

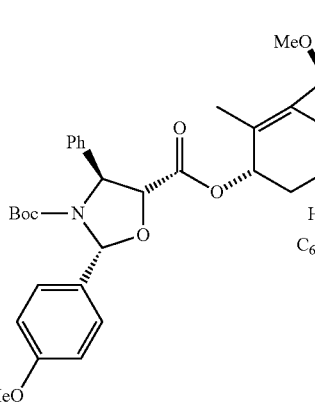

[Chemical Formula 8]

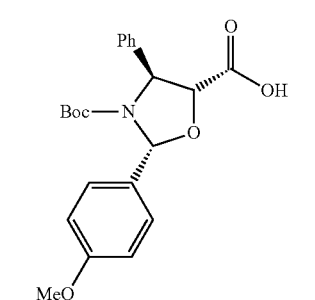

[Chemical Formula 1]

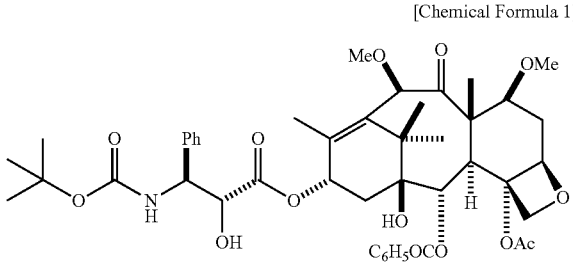

in the above formulas,
Ac represents acetyl group;
Me represents methyl group;
Ph represents phenyl group; and
M represents a silylated radical.

According to another aspect of the present invention, a compound of the following Chemical Formula 4 is provided:

[Chemical Formula 4]

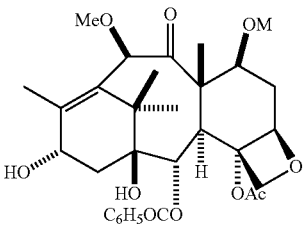

in the above Chemical Formula 4,
Ac represents acetyl group;
Me represents methyl group; and
M represents a silylated radical.

Advantageous Effects of Invention

The method for preparing cabazitaxel according to an embodiment of the present invention can efficiently curtail the reaction time by the use of 10-deacetylbaccatin III as a starting material, and the reaction via the intermediate of Chemical Formula 3—in which hydroxyl group at the 7 position is selectively protected by a silylated radical—and the intermediate of Chemical Formula 4 which is obtained by subsequent alkylation of hydroxy group at the 10 position. In each step, each intermediate can be obtained in high yield through crystallization without a separate purification by chromatography. As a result, an embodiment of the present invention can curtail the overall process time and at the same time remarkably improve the yield of the target compound, and thus is very economical and can be properly applied to the production of cabazitaxel on an industrial scale. According to an embodiment of the present invention, cabazitaxel with a high purity of 70-90% can be easily and efficiently obtained with a high yield of 20-40%.

MODE FOR THE INVENTION

The present invention is described in detail hereinafter.

The method for preparing cabazitaxel according to an embodiment of the present invention is schematically represented in the following:

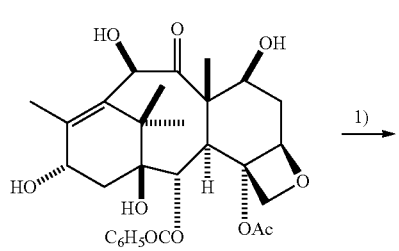

2 (10-deacetylbaccatin III)

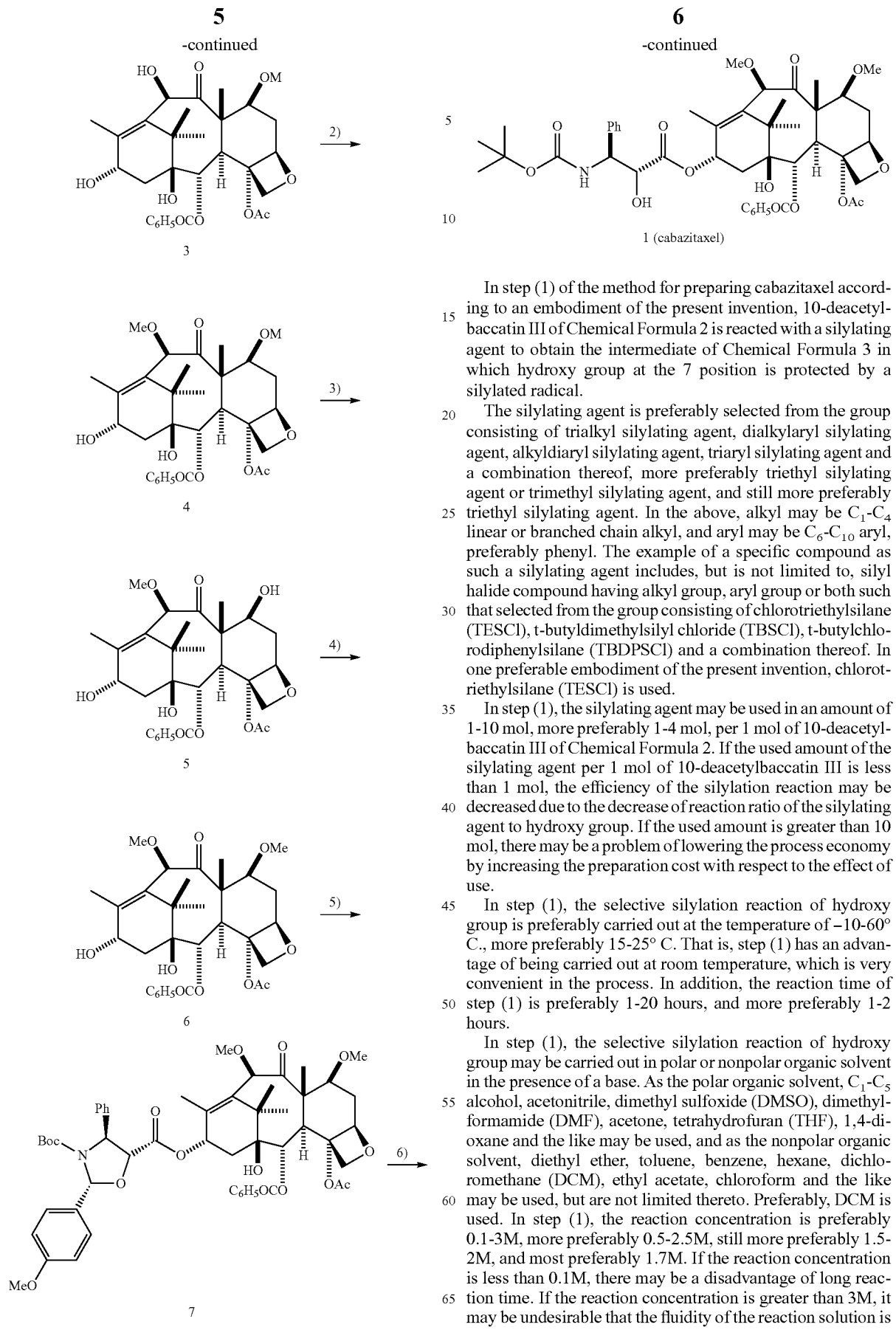

In step (1) of the method for preparing cabazitaxel according to an embodiment of the present invention, 10-deacetylbaccatin III of Chemical Formula 2 is reacted with a silylating agent to obtain the intermediate of Chemical Formula 3 in which hydroxy group at the 7 position is protected by a silylated radical.

The silylating agent is preferably selected from the group consisting of trialkyl silylating agent, dialkylaryl silylating agent, alkyldiaryl silylating agent, triaryl silylating agent and a combination thereof, more preferably triethyl silylating agent or trimethyl silylating agent, and still more preferably triethyl silylating agent. In the above, alkyl may be $C_1$-$C_4$ linear or branched chain alkyl, and aryl may be $C_6$-$C_{10}$ aryl, preferably phenyl. The example of a specific compound as such a silylating agent includes, but is not limited to, silyl halide compound having alkyl group, aryl group or both such that selected from the group consisting of chlorotriethylsilane (TESCl), t-butyldimethylsilyl chloride (TBSCl), t-butylchlorodiphenylsilane (TBDPSCl) and a combination thereof. In one preferable embodiment of the present invention, chlorotriethylsilane (TESCl) is used.

In step (1), the silylating agent may be used in an amount of 1-10 mol, more preferably 1-4 mol, per 1 mol of 10-deacetylbaccatin III of Chemical Formula 2. If the used amount of the silylating agent per 1 mol of 10-deacetylbaccatin III is less than 1 mol, the efficiency of the silylation reaction may be decreased due to the decrease of reaction ratio of the silylating agent to hydroxy group. If the used amount is greater than 10 mol, there may be a problem of lowering the process economy by increasing the preparation cost with respect to the effect of use.

In step (1), the selective silylation reaction of hydroxy group is preferably carried out at the temperature of −10-60° C., more preferably 15-25° C. That is, step (1) has an advantage of being carried out at room temperature, which is very convenient in the process. In addition, the reaction time of step (1) is preferably 1-20 hours, and more preferably 1-2 hours.

In step (1), the selective silylation reaction of hydroxy group may be carried out in polar or nonpolar organic solvent in the presence of a base. As the polar organic solvent, $C_1$-$C_5$ alcohol, acetonitrile, dimethyl sulfoxide (DMSO), dimethylformamide (DMF), acetone, tetrahydrofuran (THF), 1,4-dioxane and the like may be used, and as the nonpolar organic solvent, diethyl ether, toluene, benzene, hexane, dichloromethane (DCM), ethyl acetate, chloroform and the like may be used, but are not limited thereto. Preferably, DCM is used. In step (1), the reaction concentration is preferably 0.1-3M, more preferably 0.5-2.5M, still more preferably 1.5-2M, and most preferably 1.7M. If the reaction concentration is less than 0.1M, there may be a disadvantage of long reaction time. If the reaction concentration is greater than 3M, it may be undesirable that the fluidity of the reaction solution is lowered, and the reaction may not be carried out uniformly.

As the base, pyridine, pyrimidine, triethylamine, diethylamine, isopropylamine, N,N-dimethylaminopyridine (DMAP), diisopropylamine (DIPA), N,N-diisopropylethylamine (DIPEA) and the like may be used, but are not limited thereto. Preferably, DMAP is used. In step (1), the base is preferably used in an amount of 1-10 mol, more preferably 2-7 mol, still more preferably 3-6 mol, and most preferably 5 mol, per 1 mol of 10-deacetylbaccatin III. If the used amount of the base per 1 mol of 10-deacetylbaccatin III is less than 1 mol, the amount of impurity is increased at the time of completing the reaction, and the reaction may not be terminated due to a slow reaction rate. If the used amount is greater than 10 mol, unwanted by-product may be generated due to overreaction, and it may be undesirable that the removal of excess base after completing the reaction is difficult.

In step (1), after completing the reaction the intermediate of Chemical Formula 3 may be obtained via a crystallization method and then be used in the next step without a separate purification.

In an embodiment of the present invention, the crystallization of the intermediates and the target compound may be carried out according to conventional methods (e.g., precipitation and crystal formation method) in the art. For example, after a reaction is completed, a crude compound—which is obtained via a conventional workup method—is precipitated by the use of a solvent and/or anti-solvent for crystallization to form a precipitate. As the solvent, ethyl acetate, acetone, $C_1$-$C_4$ linear or branched chain alcohol, tetrahydrofuran, dichloromethane (DCM), chloroform, toluene, diethyl ether, 1,4-dioxane, acetonitrile, dimethylformamide (DMF), dimethyl sulfoxide (DMSO), acetic acid, formic acid and the like may be used alone or in combination, but are not limited thereto. As the anti-solvent, hexane, water, or aqueous solution of inorganic salt such as $NH_4Cl$ aqueous solution or NaCl aqueous solution and the like may be used alone or in combination, but are not limited thereto. Without limitation thereto, according to one preferable embodiment of the present invention the synthesized crude compound is dissolved in DCM, and the DCM solution is then added dropwise to excess hexane to obtain crystal. At this time, the volume ratio of solvent to anti-solvent is 1:2-1:20, preferably 1:5-1:10. The precipitate is formed according to the above method, and it is then filtrated and dried to obtain crystal.

The method for preparing cabazitaxel according to an embodiment of the present invention can curtail the synthesis time, minimize the amount of reagents used in the reaction, perform effective reaction within a short time, and save on the preparation cost by the use of 10-deacetylbaccatin III as a starting material, and the intermediate of Chemical Formula 3—in which hydroxy group at the 7 position is selectively protected by a silylated radical—is obtained as the above step (1), and the reaction is carried out via the intermediate of Chemical Formula 4 which is obtained by alkylation of hydroxy group at the 10 position in step (2) stated below. In addition, because the reaction resultant can be obtained by a crystallization method, the purity is high, and the yield is remarkably improved by preventing material loss which may be possible in the process of chromatographic purification.

In step (2) of the method for preparing cabazitaxel according to an embodiment of the present invention, the intermediate of Chemical Formula 4 is obtained by methylating hydroxy group at the 10 position of the intermediate of Chemical Formula 3 obtained as above.

In step (2), the methylation of hydroxy group may be carried out by the use of a methylating agent. The preferable methylating agent may be one or more selected from the group consisting of dimethyl sulfate ($Me_2SO_4$), methyl iodide (MeI), trimethyloxonium tetrafluoroborate, and more preferably dimethyl sulfate. In step (2), the methylating agent may be preferably used in an amount of 1-10 mol, and more preferably 2-4 mol, per 1 mol of the intermediate of Chemical Formula 3. If the used amount of the methylating agent per 1 mol of the intermediate of Chemical Formula 3 is less than 1 mol, there may a problem that the reaction is insufficient. If the used amount is greater than 10 mol, there may be a problem of lowering yield and purity by increasing impurities due to progress of overreaction, and residual excess reagents may make purification difficult.

The methylation reaction of step (2) may be carried out according to a known alkylation reaction—for example, under alkylation condition disclosed in International Publication No. WO 96/30355. Specifically, the alkylation reaction may be carried out at the temperature of −30° C. to −10° C. in the presence of a methylating agent such as $Me_2SO_4$ by the addition of strong base such as NaH. The strong base such as NaH may be preferably used in an amount of 1-20 mol, and more preferably 4-6 mol, per 1 mol of the intermediate of Chemical Formula 3 used therein. The reaction temperature is preferably −40° C. to 60° C., and more preferably −20° C. to 0° C. If the reaction temperature is lower than −40° C., there may be a problem that the reaction is insufficient. If the reaction temperature is higher than 60° C., it may be problematic of increasing unwanted impurities due to overreaction.

In step (2), after the reaction is completed, the intermediate of Chemical Formula 4 may be obtained according to the crystallization method as explained above, and then it may be used in the next step without separate purification.

In an embodiment of the present invention, the compound of Chemical Formula 4 obtained as an intermediate is novel, and provided according to another aspect of the present invention.

In step (3) of the method for preparing cabazitaxel according to an embodiment of the present invention, the intermediate of Chemical Formula 5 is obtained by deprotecting hydroxy group at the 7 position of the intermediate of Chemical Formula 4 obtained as above.

In step (3), the deprotection reaction of hydroxy group may be carried out by the use of acid. The example of the acid includes inorganic acid such as hydrohalic acid, sulfuric acid, nitric acid, phosphoric acid, sulfamic acid, perchloric acid, chromic acid, sulfurous acid, nitrous acid and the like; organic acid such as halogenated acid, formic acid, acetic acid, oxalacetic acid, propionic acid, oxalic acid, glycolic acid, tartaric acid, citric acid, fumaric acid, malic acid, succinic acid, butyric acid, trifluoroacetic acid and the like; or a mixture thereof. In step 3, the deprotection may be carried out by adding such an acid or a mixture of acid and organic solvent dropwise to the reaction solution. The organic solvent is preferably $C_1$-$C_4$ linear or branched chain alcohol. In one preferable embodiment of the present invention, a mixed solution of halogenated acid (e.g., hydrochloric acid) and $C_1$-$C_4$ linear or branched chain alcohol (e.g., ethanol or methanol) is used for deprotection.

In the case of carrying out deprotection by the use of a mixed solution of acid and organic solvent, the volume ratio of acid to organic solvent included therein is preferably 1:0.5 to 1:10, and more preferably 1:2 to 1:4, but is not limited thereto.

In step (3), the deprotection reaction may be carried out at the temperature of preferably −10 to 30° C., and more preferably 0 to 25° C. If the temperature of the deprotection reaction is lower than −10° C., there may be a problem that the reaction is insufficient. If the temperature is higher than 30° C., it may be problematic of increasing unwanted impurities due to overreaction.

In step (3), after the reaction is completed, the intermediate of Chemical Formula 5 may be obtained according to the crystallization method as explained above, and then it may be used in the next step without separate purification.

In step (4) of the method for preparing cabazitaxel according to an embodiment of the present invention, the intermediate of Chemical Formula 6 is obtained by methylating hydroxy group at the 7 position of the intermediate of Chemical Formula 5 obtained as above.

In step (4), the methylation of hydroxy group may be carried out by the use of a methylating agent as explained in step (2), and the reaction condition for methylation is also the same as that explained in step (2).

In step (4), after the reaction is completed, the intermediate of Chemical Formula 6 may be obtained according to the crystallization method as explained above, and then it may be used in the next step without separate purification.

In step (5) of the method for preparing cabazitaxel according to an embodiment of the present invention, the intermediate of Chemical Formula 7 is obtained by esterifying hydroxy group at the 13 position of the intermediate of Chemical Formula 6 obtained as above in the presence of oxazolidine acid derivative of Chemical Formula 8.

In step (5), esterification of hydroxy group of the 13 position in the presence of oxazolidine acid derivative may be carried out by a known esterification method using such compounds—for example, the esterification method in the presence of oxazolidine acid according to the method disclosed in WO 96/30355 mentioned above.

More specifically, the compound of Chemical Formula 7 may be prepared by the condensation reaction of the compound of Chemical Formula 6 and oxazolidine acid derivative of Chemical Formula 8.

[Chemical Formula 8]

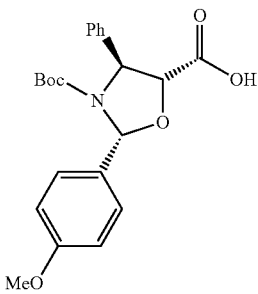

At this time, oxazolidine acid derivative of Chemical Formula 8 may be preferably used in an amount of 1-2 equivalents, and more preferably 1.2-1.5 equivalents, based on 1 equivalent of the compound of Chemical Formula 6. If the used amount is less than 1 equivalent based on 1 equivalent of the compound of Chemical Formula 6, the reaction may be insufficient. If the used amount is greater than 2 equivalents, it is economically undesirable since expensive reagent is added over the amount required for the reaction. In the condensation reaction of this step, as a condensing agent, one or more selected from dicyclohexylcarbodiimide (DCC), diisopropylcarbodiimide (DIC) and ethyl-3-(3-dimethylaminopropyl)carbodiimide (EDC) may be used, but are not limited thereto. Preferably, inexpensive dicyclohexylcarbodiimide may be used. The condensing agent may be preferably used in an amount of 1-4 equivalents, and more preferably 1.7-2.2 equivalents, based on 1 equivalent of the compound of Chemical Formula 6. If the used amount is less than 1 equivalent based on 1 equivalent of the compound of Chemical Formula 6, the reaction may be insufficient. If the used amount is greater than 4 equivalents, the preparation cost may be increased due to over-addition of the reagent, and the generation of by-product such as urea in a large amount may make purification difficult. The example of the solvent useful in the reaction of this step includes, but is not limited to, ethyl acetate, methyl acetate, dichloromethane, toluene, xylene, tetrahydrofuran and the like. Preferably, ethyl acetate, which is environmentally friendly, may be used.

In the reaction of this stage, an activator may be additionally used. As the activator, amines such as 4-dimethylaminopyridine (DMAP), pyridine and the like may be used alone or in combination of two kinds or more, but is not limited thereto. The activator may be preferably used under a stoichiometric equivalent—for example, in an amount of 0.3-0.5 equivalent based on 1 equivalent of the compound of Chemical Formula 6. If the used amount is less than 0.3 equivalent based on 1 equivalent of the compound of Chemical Formula 6, the reaction may be insufficient. If the used amount is greater than 0.5 equivalent, there may be a possibility that the generation of by-product in a large amount makes purification difficult.

The reaction temperature of this step is preferably 0-60° C., and more preferably 20-30° C. If the reaction temperature is lower than 0° C., there may be a problem that the reaction does not proceed or the reaction time is too long. If the reaction temperature is higher than 60° C., purity may be lowered due to the increase of by-product generation. The reaction time of this step is preferably 1-5 hours. If the reaction time is less than 1 hour, the target compound may not be sufficiently prepared. If the reaction time is greater than 5 hours, generation of by-product may be increased.

In step (5), after reaction termination, the intermediate of Chemical Formula 7 may be obtained according to the crystallization method as explained above, and then it may be used in the next step without separate purification.

In step (6) of the method for preparing cabazitaxel according to an embodiment of the present invention, cabazitaxel is obtained by treating the intermediate of Chemical Formula 7 obtained as above with an acid to deprotect hydroxy group of the 10 position.

In step (6), the deprotection of hydroxy group of 10 position may be carried out by the use of an acid as explained in step (3), and reaction condition for deprotection is also the same as that explained in step (3).

After the reaction of step (6) is terminated, cabazitaxel in the form of dry solid is obtained by the crystallization method as explained above.

The obtained dry solid may be easily further purified according to conventional methods in the art such as column chromatography.

In the method of an embodiment of the present invention, each step can progress to the next step without chromatographic purification. Therefore, because each intermediate can be obtained without a process of chromatographic purification, the method of an embodiment of the present invention is very economical and advantageous in industrial-scale production by simplifying the synthetic process. In addition, the method of an embodiment of the present invention can prevent various losses of materials which may occur during chromatographic purification (e.g., loss may occur in the course of dissolving and filtrating to prepare a purification step, loss may occur by adsorbing part of materials to column packing materials, and loss may occur by remaining materials on the wall of vessels during transfer between vessels) so as to show the effect of remarkably increased yield.

As such, in the method for preparing cabazitaxel of an embodiment of the present invention, the intermediates obtained in each step can be used in the next step without separate purification. However, the intermediates may be used after further purification. Therefore, the method for preparing cabazitaxel of an embodiment of the present invention may further comprise one or more steps for purifying the obtained material in each step or overall steps.

According to one preferable embodiment of the present invention, high purity of 70-90% cabazitaxel dry solid can be prepared with the high yield of about 20-40% based on starting material, 10-deacetylbaccatin III.

Hereinafter, the present invention is explained in more detail with the following examples. However, it must be understood that the protection scope of the present invention is not limited to the examples.

ABBREVIATIONS

TESCl: triethylsilyl chloride
DCM: dichloromethane
EA: ethyl acetate
sat. NaCl: saturated sodium chloride
conc. HCl: concentrated hydrochloric acid
DMAP: 4-dimethylaminopyridine
NaH: sodium hydride
THF: tetrahydrofuran
MeOH: methanol
DMF: N,N-dimethylformamide
DCC: N,N'-dicyclohexylcarbodiimide
TLC: thin-layer chromatography (TLC mobile phase solution: hexane/ethyl acetate=1/2)
HPLC: high-performance liquid chromatography

EXAMPLE

1) Preparation of Intermediate of Chemical Formula 3

100 g of 10-deacetylbaccatin III was dissolved in 550 ml of DCM, and 100 g of DMAP and 35 ml of TESCl were then added thereto. After agitation of the reaction mixture for 2 hours, the reaction completion was confirmed by TLC, and 5% $NH_4Cl$ was added to perform extraction. The obtained organic layer after extraction was dried with $MgSO_4$, filtrated and concentrated. The concentrated solution was dissolved in 0.1 L of acetone, and 1 L of hexane was then added thereto to form a precipitate. After completion of hexane addition, the reaction mixture was additionally agitated for 30 minutes, filtrated and dried under reduced pressure in a 40° C. oven to obtain 130 g of the intermediate of Chemical Formula 3 as a white solid. The purity of the obtained dry solid was 93% (HPLC).

2) Preparation of Intermediate of Chemical Formula 4

130 g of the obtained intermediate of Chemical Formula 3 was dissolved in 2.8 L of THF, the resulting solution was cooled to −20° C., and 59 ml of $Me_2SO_4$ was added thereto. Then, 40 g of NaH (60% dispersion in mineral oil) was slowly added thereto, and the resulting mixture was agitated for about 2 hours. The reaction completion was confirmed by HPLC, and sat. $NH_4Cl$ and DCM were added to perform extraction. The obtained DCM layer was dried with $MgSO_4$, filtrated and concentrated. The concentrated solution was dissolved in 0.1 L of DCM, and 1 L of hexane was added thereto to form a precipitate. After completion of hexane addition, the reaction mixture was additionally agitated for 30 minutes, filtrated and dried under reduced pressure in a 40° C. oven to obtain 124 g of the intermediate of Chemical Formula 4 as a white solid (purity: 82%).

Intermediate of Chemical Formula 4

$^1H$ NMR (400 MHz, $CDCl_3$) δ 8.10 (d, J=7.1 Hz, 2H), 7.59 (t, J=7.4 Hz, 1H), 7.46 (t, J=7.7 Hz, 2H), 5.60 (d, J=7.0 Hz, 1H), 4.99-4.87 (m, 3H), 4.43 (dd, J=10.5, 6.7 Hz, 1H), 4.30 (d, J=8.1 Hz, 1H), 4.14 (d, J=8.3, Hz, 1H), 3.88 (d, J=6.6 Hz, 1H), 3.41 (s, 3H), 2.52-2.45 (m, 1H), 2.28 (s, 3H), 2.26 (s, 1H), 2.11 (s, 3H), 2.08 (d, J=5.1 Hz, 1H), 1.92-1.85 (m, 1H), 1.67 (s, 3H), 1.59 (s, 1H), 1.58 (s, 1H), 1.17 (s, 3H), 1.07 (s, 3H), 0.96 (t, J=7.9 Hz, 9H), 0.65-0.50 (m, 6H);
$^{13}C$ NMR (75 MHz, $CDCl_3$) δ 204.60, 170.97, 167.21, 143.07, 134.02, 133.68, 130.24, 129.61, 128.69, 84.47, 82.83, 81.19, 78.96, 77.23, 74.98, 73.10, 68.20, 58.40, 55.96, 47.48, 43.02, 38.49, 37.49, 27.01, 22.89, 19.72, 15.34, 10.04, 6.95, 5.58;
LRMS (ESI) m/z 695.7 $(M+Na)^+$

3) Preparation of Intermediate of Chemical Formula 5

124 g of the obtained intermediate of Chemical Formula 4 was dissolved in 455 ml of methanol, and the resulting solution was cooled to 0° C. 455 ml of 4N HCl was slowly added thereto, and the resulting mixture was then agitated for about 2 hours. The reaction completion was confirmed by TLC, and 5.2 L of 5% $NaHCO_3$ solution was added to form a precipitate. The formed precipitate was filtrated and washed with distilled water. The obtained precipitate was dried under reduced pressure in a 40° C. oven to obtain 83 g of the intermediate of Chemical Formula 5 (purity: 75%, cumulative yield from 10-deacetylbaccatin III is 57%).

4) Preparation of Intermediate of Chemical Formula 6

83 g of the obtained intermediate of Chemical Formula 5 was dissolved in 400 ml of DMF, the resulting solution was cooled to −30° C., and 35 ml of $Me_2SO_4$ was added thereto. Then, 14 g of NaH (60% dispersion in mineral oil) was slowly added thereto, and the resulting mixture was agitated for about 1 hour. The reaction completion was confirmed by HPLC, and 4 L of 5% $NH_4Cl$ aqueous solution was slowly added to form a precipitate. The obtained precipitate was filtrated, washed with excess distilled water and dried under reduced pressure in a 40° C. oven to obtain 69 g of the intermediate of Chemical Formula 6 as a white solid (purity: 73%, yield: 79%, cumulative yield from 10-deacetylbaccatin III is 45%).

5) Preparation of Intermediate of Chemical Formula 7

137 g of oxazolidine acid derivative of Chemical Formula 8 was dissolved in 2 L of EA, and 227 g of DCC and 23 g of DMAP were added thereto. To the resulting solution 69 g of the obtained intermediate of Chemical Formula 6 was added and agitated at room temperature for about 3 hours. After reaction was completed, insoluble materials were removed by filtration, and the organic phase was concentrated under reduced pressure. The concentrated solution was dissolved in 0.1 L of DCM, and 1 L of hexane was added thereto to form a precipitate. After completion of hexane addition, the reaction mixture was additionally agitated for 30 minutes, filtrated and dried under reduced pressure in a 40° C. oven to obtain 78 g of the intermediate of Chemical Formula 7 as a white solid (purity: 88%, yield: 84%, cumulative yield from 10-deacetylbaccatin III is 38%).

6) Preparation of Compound of Chemical Formula 1 (Cabazitaxel)

78 g of the obtained intermediate of Chemical Formula 7 was dissolved in 4 L of methanol and 4 L of DCM, and the resulting solution was cooled to 0° C. 78 ml of 1N HCl was slowly added thereto, and the resulting mixture was then agitated for about 1 hour. Sat. NH$_4$Cl and DCM were added thereto to perform extraction. The obtained DCM layer was dried with MgSO$_4$, filtrated and concentrated. The concentrated solution was dissolved in 0.1 L of methanol, and 1.2 L of distilled water was added thereto to form a precipitate. After completion of distilled water addition, the reaction mixture was additionally agitated for 30 minutes, filtrated and dried under reduced pressure in a 40° C. oven to obtain 59 g of cabazitaxel dry solid as a white solid (purity: 90%). From HPLC analysis, cabazitaxel content of the obtained dry solid is 72%, and the total yield from starting material, 10-deacetylbaccatin III, to the dry solid containing cabazitaxel is 28%.

Compound of Chemical Formula 1 (Cabazitaxel)

$^1$H NMR (400 MHz, CDCl$_3$) δ 8.09 (d, J=7.2 Hz, 2H), 7.60 (t, J=7.4 Hz, 1H), 7.48 (t, J=7.6 Hz, 2H), 7.35-7.30 (m, 5H), 6.21 (t, J=8.6 Hz, 1H), 5.63 (d, J=7.2 Hz, 1H), 5.45 (d, J=9.6 Hz, 1H), 5.27 (d, J=8.4 Hz, 1H), 4.97 (d, J=7.6 Hz, 1H), 4.79 (s, 1H), 4.62 (s, 1H), 4.29 (d, J=8.4 Hz, 1H), 4.17 (d, J=8.4 Hz, 1H), 3.88-3.80 (m, 2H), 3.45 (s, 3H), 3.30 (s, 3H), 2.73-2.66 (m, 1H), 2.36 (s, 3H), 2.31-2.27 (m, 2H), 1.87 (s, 3H), 1.83-1.76 (m, 1H), 1.71 (s, 3H), 1.36 (s, 9H), 1.25 (s, 1H), 1.21 (s, 3H), 1.20 (s, 3H);
$^{13}$C NMR (75 MHz, CDCl$_3$) δ 204.94, 172.69, 170.43, 166.97, 155.30, 138.67, 138.36, 135.61, 133.64, 129.18, 128.81, 128.64, 128.05, 126.83, 84.09, 82.64, 81.75, 80.75, 80.23, 78.73, 77.23, 74.52, 73.69, 72.56, 57.34, 57.04, 56.91, 56.18, 47.39, 43.29, 35.22, 32.12, 28.21, 26.83, 22.69, 20.68, 14.64, 10.34; LRMS (ESI) m/z 858.7 (M+Na)$^+$

As can be seen from the above, in the case of preparing cabazitaxel according to an embodiment of the present invention, the total yield from starting material, 10-deacetylbaccatin III, to the dry solid containing cabazitaxel is 28%. Such yield is remarkably improved as compared with that of the method disclosed in International Publication No. WO 96/30355 in which the total yield of preparing cabazitaxel is about 4%.

In addition, the reaction time of steps (1) to (3) in the above Example of the present invention is compared with that of the method disclosed in WO 96/30355 as follows:

| Synthesis step | Reaction time | |
| --- | --- | --- |
| | WO 96/30355 | Example |
| Step 1 | 3 hours | about 2 hours |
| Step 2 | 25 hours | about 2 hours |
| Step 3 | 48 hours | about 2 hours |

As can be seen from the above, according to an embodiment of the present invention, cabazitaxel can be prepared with a remarkably improved yield within a markedly short time as compared with the conventional method for preparing cabazitaxel.

The invention claimed is:

1. A method for preparing cabazitaxel comprising the steps of:
   1) reacting 10-deacetylbaccatin III of Chemical Formula 2 with a silylating agent to obtain an intermediate of Chemical Formula 3 in which hydroxy group at the 7 position is protected by a silylated radical;
   2) methylating hydroxy group at the 10 position of the intermediate of Chemical Formula 3 to obtain an intermediate of Chemical Formula 4;
   3) deprotecting hydroxy group at the 7 position of the intermediate of Chemical Formula 4 to obtain an intermediate of Chemical Formula 5;
   4) methylating hydroxy group at the 7 position of the intermediate of Chemical Formula 5 to obtain an intermediate of Chemical Formula 6;
   5) esterifying hydroxy group at the 13 position of the intermediate of Chemical Formula 6 in the presence of oxazolidine acid derivative of Chemical Formula 8 to obtain an intermediate of Chemical Formula 7; and
   6) treating the intermediate of Chemical Formula 7 with an acid to obtain cabazitaxel of Chemical Formula 1:

[Chemical Formula 2]

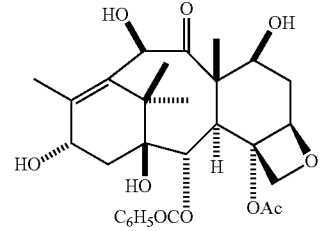

[Chemical Formula 3]

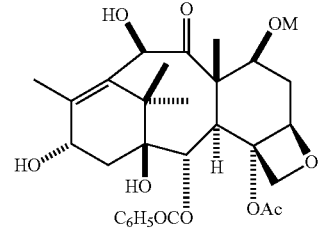

[Chemical Formula 4]

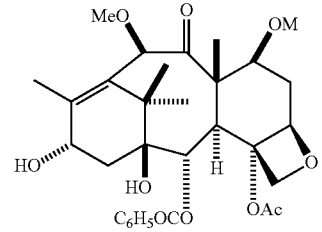

-continued

[Chemical Formula 5]

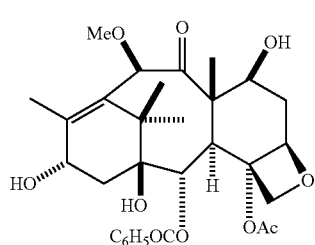

[Chemical Formula 6]

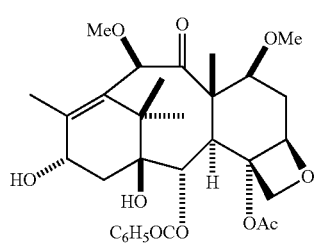

[Chemical Formula 7]

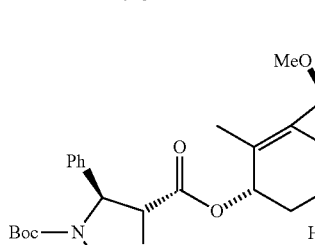

[Chemical Formula 8]

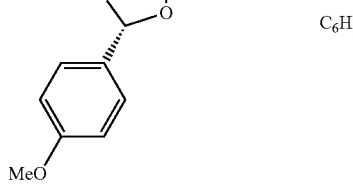

[Chemical Formula 1]

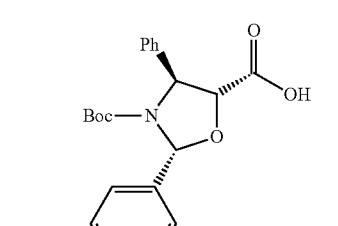

wherein
Ac represents acetyl group;
Me represents methyl group;
Ph represents phenyl group; and
M represents a silylated radical.

2. The method for preparing cabazitaxel according to claim 1, wherein the silylating agent is selected from the group consisting of trialkyl silylating agent, dialkylaryl silylating agent, alkyldiaryl silylating agent, triaryl silylating agent and a combination thereof,
wherein alkyl is $C_1$-$C_4$ linear or branched chain alkyl, and aryl is $C_6$-$C_{10}$ aryl.

3. The method for preparing cabazitaxel according to claim 1, wherein the silylating agent is selected from the group consisting of chlorotriethylsilane, t-butyldimethylsilyl chloride, t-butylchlorodiphenylsilane and a combination thereof.

4. The method for preparing cabazitaxel according to claim 1, wherein the silylation reaction is carried out in polar or nonpolar organic solvent in the presence of a base.

5. The method for preparing cabazitaxel according to claim 4, wherein the polar organic solvent is selected from the group consisting of $C_1$-$C_5$ alcohol, acetonitrile, dimethyl sulfoxide, dimethylformamide, acetone, tetrahydrofuran, 1,4-dioxane and a combination thereof, and the nonpolar organic solvent is selected from the group consisting of diethyl ether, toluene, benzene, hexane, dichloromethane, ethyl acetate, chloroform and a combination thereof.

6. The method for preparing cabazitaxel according to claim 4, wherein the base is selected from the group consisting of pyridine, pyrimidine, triethylamine, diethylamine, isopropylamine, N,N-dimethylaminopyridine, diisopropylamine, diisopropylethylamine and a combination thereof.

7. The method for preparing cabazitaxel according to claim 1, wherein the methylation of hydroxy group is carried out by the use of one or more methylating agents selected from the group consisting of dimethyl sulfate, methyl iodide and trimethyloxonium tetrafluoroborate.

8. The method for preparing cabazitaxel according to claim 1, wherein the deprotection reaction of hydroxy group is carried out by the use of acid, or a mixture of acid and organic solvent.

9. The method for preparing cabazitaxel according to claim 8, wherein the acid is selected from the group consisting of hydrohalic acid, sulfuric acid, nitric acid, phosphoric acid, sulfamic acid, perchloric acid, chromic acid, sulfurous acid, nitrous acid, halogenated acid, formic acid, acetic acid, oxalacetic acid, propionic acid, oxalic acid, glycolic acid, tartaric acid, citric acid, fumaric acid, malic acid, succinic acid, butyric acid, trifluoroacetic acid and a combination thereof.

10. The method for preparing cabazitaxel according to claim 8, wherein the organic solvent is $C_1$-$C_4$ linear or branched chain alcohol.

11. The method for preparing cabazitaxel according to claim 1, wherein the intermediates of each step in steps (1) to (5) are obtained by a crystallization method and used in the next step without separate purification.

12. The method for preparing cabazitaxel according to claim 1, which further comprises one or more steps of purifying a material obtained in each step.

13. A compound of Chemical Formula 4:

[Chemical Formula 4]

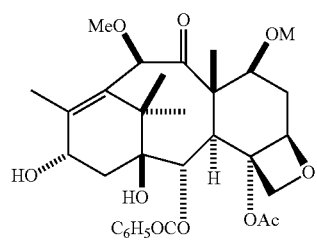

wherein

Ac represents acetyl group;

Me represents methyl group; and

M represents a silylated radical.

14. The compound according to claim 13, wherein M is trialkylsilyl, dialkylarylsilyl, alkyldiarylsilyl or triarylsilyl, wherein alkyl is $C_1$-$C_4$ linear or branched chain alkyl, and aryl is $C_6$-$C_{10}$ aryl.

* * * * *